(12) United States Patent
Patel et al.

(10) Patent No.: US 8,981,158 B2
(45) Date of Patent: Mar. 17, 2015

(54) OXIDATION OF CYCLOHEXYLBENZENE

(71) Applicant: ExxonMobil Chemical Company—Law Technology, Baytown, TX (US)

(72) Inventors: Bryan A. Patel, Arlington, VA (US); Francisco M. Benitez, Cypress, TX (US); Charles Morris Smith, Houston, TX (US); Jihad M. Dakka, Whitehouse Station, NJ (US); Travis A. Reine, Slidell, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 14/362,263

(22) PCT Filed: Nov. 2, 2012

(86) PCT No.: PCT/US2012/063375
§ 371 (c)(1),
(2) Date: Jun. 2, 2014

(87) PCT Pub. No.: WO2013/095791
PCT Pub. Date: Jun. 27, 2013

(65) Prior Publication Data
US 2014/0336417 A1  Nov. 13, 2014

Related U.S. Application Data

(60) Provisional application No. 61/577,295, filed on Dec. 19, 2011.

(51) Int. Cl.
*C07C 45/27* (2006.01)
*C07C 37/50* (2006.01)
*C07C 407/00* (2006.01)
*C07C 37/08* (2006.01)
*C07C 45/53* (2006.01)

(52) U.S. Cl.
CPC ............ *C07C 407/00* (2013.01); *C07C 37/08* (2013.01); *C07C 45/53* (2013.01); *C07C 2101/14* (2013.01); *C07C 37/50* (2013.01); *C07C 45/27* (2013.01)
USPC ............................ 568/376; 568/568; 568/798

(58) Field of Classification Search
USPC .......................................... 568/376, 568, 798
See application file for complete search history.

(56) References Cited

U.S. PATENT DOCUMENTS

| 6,037,513 | A | 3/2000 | Chang et al. |
| 2010/0234589 | A1 | 9/2010 | Dakka et al. |

FOREIGN PATENT DOCUMENTS

| WO | 2009/134514 | 11/2009 |
| WO | 2010/098916 | 9/2010 |
| WO | 2011/100013 | 8/2011 |

OTHER PUBLICATIONS

R. A. Sheldon et al., I.W.C.E. Arends, "Organocatalytic Oxidations Mediated by Nitroxyl Radicals", Advanced Synthesis & Catalysis, vol. 346, Sep. 21, 2004, (XP-002683500), pp. 1051-1071.
Isabel W.C.E. Arends et al., "Selective catalytic oxidation of cyclohexylbenzene to cyclohexylbenzene-l-hydroperoxide: a coproduct-free route to phenol", Tetrahedron, vol. 58, (2002) pp. 9055-9061.

*Primary Examiner* — Sikarl Witherspoon
(74) *Attorney, Agent, or Firm* — Jamie L. Sullivan; Siwen Chen (57) ABSTRACT

In a process for oxidizing cyclohexylbenzene, a composition comprising cyclohexylbenzene is contacted with oxygen in at least one oxidation zone under oxidation conditions sufficient to produce at least some (i) cyclohexylbenzene hydroperoxide; (ii) a first byproduct; and (iii) a second byproduct in an effluent. A ratio $\beta$ is determined according to the following formula:

$$\beta = \frac{A}{B}$$

wherein A is the amount of the first byproduct in the effluent and B is the amount of the second byproduct in the effluent. The ratio $\beta$ is then maintained above a threshold value or adjusted above a threshold value.

25 Claims, 2 Drawing Sheets

Fig. 1A

105 °C, 0 psig, 21% $O_2$, 1000 ppm NHPI

Fig. 1B

105 °C, 0 psig, 15% $O_2$, 1000 ppm NHPI

OXIDATION OF CYCLOHEXYLBENZENE

PRIORITY CLAIM TO RELATED APPLICATIONS

This application is a National Stage Application of International Application No. PCT/US2012063375 filed Nov. 2, 2012, which claims priority to and the benefit of U.S. Provisional Application Ser. No. 61/577,295 filed Dec. 19, 2011 and European Application No. 12154898.6 filed Feb. 10, 2012, the disclosures of which are fully incorporated herein by their reference.

FIELD

The present invention relates to a process for oxidizing cyclohexylbenzene.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide, and then cleavage of the hydroperoxide to produce equimolar amounts of phenol and acetone.

Another process involves the hydroalkylation of benzene to produce cyclohexylbenzene, followed by the oxidation of the cyclohexylbenzene (CHB) to cyclohexylbenzene hydroperoxide (CHBHP), which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal and a molecular sieve of the MCM-22 family.

The oxidation of CHB is a gas-liquid reaction involving mass transfer of oxygen from the feed gas (e.g., air) into the liquid CHB where it reacts to form the CHBHP. In this reaction, sufficient distribution of dissolved oxygen is important to achieving the desired CHB conversion rate and selectivity to CHBHP. That said, one challenge is that the dissolved oxygen distribution cannot be effectively measured in existing liquid phase oxidation reactors.

Gas phase oxygen detectors are known and can be used to provide information about the overall consumption rate of oxygen, which implicitly describes the general effectiveness of the reactor performance. However, this technique does not provide information about the distribution of dissolved oxygen in the CHB. Furthermore, maintenance of online analytical equipment can be costly and requires regular upkeep. Lower cost methods using offline measurement are desirable.

According to the invention, it has now been discovered that the dissolved oxygen distribution is directly correlated to a ratio β, which is a ratio of at least two byproducts produced during the oxidation reaction. More specifically, it has been found that the dissolved oxygen concentration affects the amount of certain byproducts produced during the oxidation reaction. For example, at low dissolved oxygen conditions, more of certain byproducts (e.g., 1-phenyl-1-hexaphenone) are produced. At stoichiometrically sufficient or excess oxygen conditions, more of certain other byproducts (e.g., 6-hydroperoxyhexaphenone and 6-hydroxyhexaphenone) are produced. As such, a ratio of byproducts can be used to directly determine, or as a proxy for determining, the dissolved oxygen concentration in a CHB oxidation reaction.

SUMMARY

The invention relates to a process comprising:
a) contacting a composition comprising cyclohexylbenzene and oxygen in at least one oxidation zone under oxidation conditions sufficient to produce an effluent comprising at least some (i) cyclohexylbenzene hydroperoxide; (ii) a first byproduct that is indicative of a high dissolved oxygen content in the composition; and (iii) a second byproduct that is indicative of a low dissolved oxygen content in the composition;
b) determining a ratio β according to the following formula:

$$\beta = \frac{A}{B}$$

wherein A is the amount of the first byproduct in the effluent, and B is the amount of the second byproduct in the effluent; and
c) implementing an effect selected from (i) maintaining the ratio β above a threshold value; and (ii) adjusting the ratio β above a threshold value.

Conveniently, the effect is adjusting the ratio β above a threshold value, and the ratio β is adjusted by performing one or more of:
A) increasing the amount of oxygen supplied to the contacting step (a);
B) decreasing the temperature in the oxidation zone;
C) increasing agitation in the oxidation zone; and
D) increasing operating pressure of the oxidation zone to increase oxygen partial pressure in the gas phase.

The invention also relates to a process comprising:
a) contacting cyclohexylbenzene with an oxygen-containing compound in at least one oxidation zone under oxidation conditions sufficient to form an effluent comprising at least some cyclohexylbenzene hydroperoxide, 6-hydroperoxyhexaphenone, 6-hydroxyhexaphenone and 1-phenyl-1-hexaphenone;
b) measuring the concentrations of the 6-hydroperoxyhexaphenone, 6-hydroxyhexaphenone and 1-phenyl-1-hexaphenone in the effluent;
c) determining a ratio β according to the following formula:

$$\beta = \frac{[6\text{-hydroperoxyhexaphenone}] + [6\text{-hydroxyhexaphenone}]}{[1\text{-phenyl-1-hexaphenone}]};$$

wherein [6-hydroperoxyhexaphenone], [6-hydroxyhexaphenone] and [1-phenyl-1-hexaphenone] are molar concentrations of the respective components in the effluent; and
d) adjusting the ratio β to above a threshold value.

The invention also relates to a process comprising:
a) contacting benzene with hydrogen in the presence of a hydroalkylation catalyst under conditions effective to produce cyclohexylbenzene;
b) contacting at least a portion of the cyclohexylbenzene with oxygen in the presence of a cyclic imide catalyst under conditions effective to form an effluent comprising at least some cyclohexylbenzene hydroperoxide, 6-hydroperoxyhexaphenone, 6-hydroxyhexaphenone and 1-phenyl-1-hexaphenone, wherein at least a portion of the contacting step (a) is conducted at a ratio β of greater than 0.1, wherein β is determined according to the following formula:

$$\beta = \frac{[\text{6-hydroperoxyhexaphenone}] + [\text{6-hydroxyhexaphenone}]}{[\text{1-phenyl-1-hexaphenone}]};$$

where [6-hydroperoxyhexaphenone], [6-hydroxyhexaphenone], and [1-phenyl-1-hexaphenone] are molar concentrations of 6-hydroperoxyhexaphenone, 6-hydroxyhexaphenone, and 1-phenyl-1-hexaphenone respectively in the effluent; and c) cleaving at least a portion of the cyclohexylbenzene hydroperoxide produced in (b) to produce phenol and cyclohexanone.

DETAILED DESCRIPTION OF THE EMBODIMENTS

Described herein is a cyclohexylbenzene oxidation process. In this process, cyclohexylbenzene and oxygen are contacted in at least one oxidation zone under oxidation conditions sufficient to produce an effluent containing at least some (i) cyclohexylbenzene hydroperoxide; (ii) a first byproduct; and (iii) a second byproduct. A ratio β that is correlated to the amount of oxygen dissolved in the composition is determined according to the following formula:

$$\beta = \frac{A}{B}$$

where A is the amount of the first byproduct in the effluent, and B is the amount of the second byproduct in the effluent. The process further comprises implementing an effect selected from (i) maintaining the ratio β above a threshold value; and (ii) adjusting the ratio β above a threshold value.

The present oxidation process may form part of an integrated process for producing phenol and cyclohexanone from benzene, in which the benzene is converted to cyclohexylbenzene, the cyclohexylbenzene is then oxidized to cyclohexylbenzene hydroperoxide, and the cyclohexylbenzene hydroperoxide is cleaved to produce phenol and cyclohexanone. The steps of this integrated process are describe in more detail below.

Hydrocarbon Feed

One step in an integrated process for producing phenol and cyclohexanone involves the production of cyclohexylbenzene by reacting benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as, less than 500 ppm, for example, less than 100 ppm, water. In addition, the total feed typically contains less than 100 ppm, such as, less than 30 ppm, for example, less than 3 ppm, sulfur and less than 10 ppm, such as, less than 1 ppm, for example, less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4:1 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example, at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Treatment of the Cyclohexylbenzene Product

Although the hydroalkylation reaction using an MCM-22 family zeolite catalyst is highly selective towards cyclohexylbenzene, the liquid effluent from the hydroalkylation reaction may contain significant quantities of unreacted benzene and certain by-products in addition to the desired cyclohexylbenzene. One of the major by-products are polycyclohexylbenzenes (di- and tricyclohexylbenzene), which typically comprise up to 20 wt % of the conversion products. These polycyclohexylbenzenes may be converted into additional useful cyclohexylbenzene product.

For example, separation of the polycyclohexylbenzenes is conveniently achieved by supplying at least a portion of the reaction product to a fractionation device, normally a fractionation column, to separate the reaction product into at least a first fraction rich in cyclohexylbenzene and a second fraction rich in polycyclohexylbenzenes. In addition, to allow the separation to be effected at or near atmospheric pressure (about 100 kPa to about 300 kPa) and at relatively low temperatures, at least one $C_4$ to $C_6$ hydrocarbon in the vapor phase is supplied separately to the fractionation device, normally at or adjacent the base of the fractionation column. Although any $C_4$ to $C_6$ hydrocarbon vapor can be used, benzene vapor is particularly useful since, for example, the hydroalkylation reaction effluent contains significant quantities (typically up to 60 wt %) of unreacted benzene.

Conveniently, the $C_4$ to $C_6$ hydrocarbon vapor is supplied to the fractionation device at a temperature of about 190° C. to about 300° C. More particularly, where steam is used to heat and vaporize the $C_4$ to $C_6$ hydrocarbon, the temperature of the $C_4$ to $C_6$ hydrocarbon vapor supplied to the fractionation device is between about 190° C. and about 241° C. Generally, the ratio of the weight of the $C_4$ to $C_6$ hydrocarbon vapor supplied to the fractionation device to the weight of the reaction product supplied to the fractionation device is from about 0.05:1 to about 2:1, such as from about 0.1:1 to about 1:1, for example about 0.5:1.

In one embodiment of the present process, after separation from the hydroalkylation reaction effluent, the polycyclohexylbenzenes are mixed with benzene and transalkylated to produce additional monocyclohexylbenzene. Transalkylation is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio 1:1 to about 5:1.

In another embodiment of the present process, conversion of the polycyclohexylbenzenes to additional monocyclohexylbenzene is effected by dealkylation. Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds, and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene-rich stream separated from the hydroalkylation reaction product is fed to the oxidation reaction described in more detail below.

Hydrocarbon Oxidation

In any embodiment, the oxidation step can be accomplished by contacting cyclohexylbenzene with oxygen, such as an oxygen-containing compound (e.g., air) under oxidation conditions to produce at an effluent containing at least some cyclohexylbenzene hydroperoxide. This may be conducted in the presence or absence of an oxidation catalyst.

In any embodiment, the oxidation step may be conducted in the presence of a catalyst comprising a cyclic imide having an imide group of formula (I):

(I)

wherein X represents an oxygen atom, a hydroxyl group, or an acyloxy group.

Generally, the cyclic imide employed as the oxidation catalyst is of the general formula II:

(II)

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

More specifically, the cyclic imide employed as the oxidation catalyst typically is of the general formula III:

(III)

wherein X represents an oxygen atom, a hydroxyl group and each of $R^7$, $R^8$, $R^9$, and $R^{10}$ is independently selected from H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I, and/or $NO_2$.

In one practical embodiment, the cyclic imide catalyst comprises N-hydroxyphthalimide (NHPI).

The oxidizing agent employed in the present oxidation process is an oxygen-containing gas, generally air. In various embodiments, the air comprises at least 18 wt % of oxygen, or at least 20 wt % of oxygen, or at least 21 wt % of oxygen based upon the total weight of the air. The air may be dried to reduce its water content to less than or equal to 0.6 wt %, such as less than or equal to 0.3 wt %, even less than or equal to 0.1 wt %. Depending on the extent of water reduction desired, drying can be effected by cooling and/or pressurization of the gas or by passing the gas through a molecular sieve drier or a combination of these two methods.

Suitable oxidation conditions include a temperature of between about 20° C. and about 150° C., such as between about 70° C. and about 150° C., such as between about 70° C. and about 130° C. and/or a pressure between about 0 kPa and about 500 kPa, such as between about 15 kPa and about 500 kPa, such as between 15 kPa to about 150 kPa. The oxidation step can be conducted in a single oxidation reactor or in a series of reactors connected in series. The oxidation reactor may be operated in a batch, semi-batch, or continuous flow manner.

In any embodiment, the oxidation step may comprise:
(a) contacting a composition comprising cyclohexylbenzene and oxygen in at least one oxidation zone under oxidation conditions sufficient to produce an effluent comprising at least some (i) cyclohexylbenzene hydroperoxide; (ii) a first byproduct that is indicative of a high dissolved oxygen content in the composition; and (iii) a second byproduct that is indicative of a low dissolved oxygen content in the composition;
(b) determining a ratio β that is correlated to the amount of oxygen dissolved in the composition according to the following formula:

$$\beta = \frac{A}{B}$$

where A is the amount of the first byproduct in the effluent, and B is the amount of the second byproduct in the effluent; and
c) implementing an effect selected from (i) maintaining the ratio β above a threshold value; and (ii) adjusting the ratio β above a threshold value.

It will further be understood that the ratio β may be expressed in inverted form (i.e., B/A), wherein it is maintained below a threshold value or adjusted below a threshold value. This inverted form is intended to be equivalent to steps (b) and (c) described above and is encompassed within any claims reciting these steps.

It will further be understood that the amount of the first byproduct and second byproduct may be expressed in any known way, (e.g., number of moles, mass basis, or as concentrations (e.g., mol/unit volume). Additionally, the amounts of the first and second byproducts may be determined at any location(s) in the effluent, such as at the outlet of the oxidation reactor.

In various embodiments, the ratio β may be adjusted to, and/or maintained at, some minimal threshold, such as greater than 0.1, or greater than 0.3, or greater than 0.5, or greater than 0.7, or greater than 1.0 for some portion or all of the contacting step (a).

For example, the ratio may be adjusted by one or more of:
(i) increasing the amount of oxygen supplied to the contacting step (a);
(ii) decreasing the temperature in the oxidation zone;
(iii) increasing the agitation in the oxidation zone; and
(iv) increasing operating pressure of the oxidation zone to increase oxygen partial pressure in the gas phase.

Where there is a plurality of reaction zones, the ratio β may be determined in any number of the reaction zones at any location.

The first byproduct and the second byproduct may be any species produced during the contacting step (a), excluding the desired product 1-phenyl-1-cyclohexyl hydroperoxide. In various embodiments, the first byproduct and/or second byproduct each include more than one species produced during the contacting step (a). For example, the first byproduct (which is indicative of a high dissolved oxygen content) may contain one or more of 6-hydroperoxyhexaphenone and 6-hydroxyhexaphenone shown below:

6-hydroperoxyhexaphenone 6-hydroxyhexaphenone

Additionally or alternatively, the second byproduct (which is indicative of a low dissolved oxygen content) may contain one or more of 1-phenyl-1-hexaphenone, 1-phenyl-1-hexenone, benzoic acid and pentanal shown below:

benzoic acid        pentanal 1-phenyl-1-hexaphenone

1-phenyl-1-hexenone

In various embodiments, the first byproduct and/or second byproduct are formed through the decomposition of the cyclohexylbenzene hydroperoxide. For example, the cyclohexylbenzene hydroperoxide can decompose to form an alkoxy radical according to reaction (1) below.

(1)

The alkyoxy radical may then undergo β-scission according to reaction (2) below, which opens the cyclohexyl ring:

(2)

The ring-opened free radical generally follows two paths, depending on the local oxygen concentration. If there is sufficient oxygen present, the radical combines with oxygen to form a peroxy radical, which ultimately forms 6-hydroperoxyhexaphenone according to reaction (3) below.

(3)

-continued

The 6-hydroperoxyhexaphenone may then decompose according to (4) below ultimately leading to 6-hydroxyhexaphenone.

(4)

In the absence of sufficient oxygen, the radical abstracts a hydrogen from another hydrocarbon to form 1-phenyl-1-hexaphenone according to (5) below.

(5)

In various embodiments, reactions 3 & 4 proceed side-by-side with reaction 5, but their relative rates are directly dependent on the liquid phase oxygen concentration.

In various embodiments, the oxidation step produces at least some 6-hydroperoxyhexaphenone, 6-hydroxyhexaphenone and 1-phenyl-1-hexaphenone (e.g., through one or more of the mechanisms described above). In certain of these embodiments, β is equal to β', wherein β' is determined according to the following formula:

$$\beta' = \frac{[\text{6-hydroperoxyhexaphenone}] + [\text{6-hydroxyhexaphenone}]}{[\text{1-phenyl-1-hexaphenone}]}$$

wherein [6-hydroperoxyhexaphenone], [6-hydroxyhexaphenone], and [1-phenyl-1-hexaphenone] are molar concentrations of 6-hydroperoxyhexaphenone, 6-hydroxyhexaphenone, and 1-phenyl-1-hexaphenone respectively in the effluent.

Using this formula to determine β', the dissolved oxygen concentration [O₂] can be directly determined according to the following rate equation:

$$\beta' = k\left(\frac{[O_2]^2}{[\text{Cyclohexylbenzene}]}\right)$$

wherein [O₂] is the molar concentration (mol/L) of the dissolved oxygen in the effluent, [cyclohexylbenzene] is the molar concentration (mol/L) of the cyclohexylbenzene in the effluent, and k is determined by the following equation:

$$k = e^{\wedge \left[\frac{15100}{T+273.15} - 30.055\right]}$$

wherein T is the temperature of the contacting step (a) in degrees Celsius.

In various embodiments, the effluent preferably has a ratio β of greater than 0.1, or greater than 0.3, or greater than 0.5, or greater than 1.

In various embodiments, the ratio β is determined at more than one location in the effluent. The ratio β may be measured real-time, e.g., using a slip stream, or offline. The ratio β may be measured on a batch, semi-continuous, or continuous basis. In any embodiment, the change in ratio β may be measured over time.

In various embodiments, the first byproduct contains more oxygen atoms than the alkoxy radical and/or the second byproduct contains the same or less number of oxygen atoms than the alkoxy radical.

In various embodiments, the oxidation step includes:

a) contacting cyclohexylbenzene with an oxygen-containing compound in at least one oxidation zone under oxidation conditions sufficient to form an effluent comprising least some cyclohexylbenzene hydroperoxide, 6-hydroperoxyhexaphenone, 6-hydroxyhexaphenone and 1-phenyl-1-hexaphenone;

b) measuring the concentrations of the 6-hydroperoxyhexaphenone, 6-hydroxyhexaphenone, and 1-phenyl-1-hexaphenone in the effluent;

c) determining a ratio β according following formula:

$$\beta = \frac{[\text{6-hydroperoxyhexaphenone}] + [\text{6-hydroxyhexaphenone}]}{[\text{1-phenyl}-\text{1-hexaphenone}]};$$

where [6-hydroperoxyhexaphenone], [6-hydroxyhexaphenone], and [1-phenyl-1-hexaphenone] are the amounts of the respective components in the effluent; and d) adjusting the ratio β to above a threshold value.

In various embodiments, the oxidation step includes:

a) contacting benzene with hydrogen in the presence of a hydroalkylation catalyst under conditions effective to produce cyclohexylbenzene;

b) contacting at least a portion of the cyclohexylbenzene with oxygen in the presence of a cyclic imide catalyst under conditions effective to form an effluent comprising least some cyclohexylbenzene hydroperoxide, 6-hydroperoxyhexaphenone, 6-hydroxyhexaphenone, and 1-phenyl-1-hexaphenone, wherein at least a portion of the contacting step (a) is conducted at a ratio β of greater than 0.1, wherein β is determined according to the following formula:

$$\beta = \frac{[\text{6-hydroperoxyhexaphenone}] + [\text{6-hydroxyhexaphenone}]}{[\text{1-phenyl}-\text{1-hexaphenone}]}.$$

where [6-hydroperoxyhexaphenone], [6-hydroxyhexaphenone], and [1-phenyl-1-hexaphenone] are molar concentrations of 6-hydroperoxyhexaphenone, 6-hydroxyhexaphenone, and 1-phenyl-1-hexaphenone respectively in the effluent; and c) cleaving at least a portion of the cyclohexylbenzene hydroperoxide produced in (b) to produce phenol and cyclohexanone.

Purification of the Oxidation Product

Typically, the product of the cyclohexylbenzene oxidation reaction contains at least 1 wt %, or at least 3 wt %, or at least 5 wt %, such as at least 10 wt %, for example at least 15 wt %, or at least 20 wt % cyclohexylbenzene hydroperoxide based upon the total weight of the oxidation reaction effluent. Generally, the oxidation reaction effluent contains no greater than 50 wt %, or no greater than 40 wt %, or no greater than 30 wt %, or no greater than 25 wt % of cyclohexylbenzene hydroperoxide based upon the total weight of the oxidation reaction effluent. The oxidation reaction effluent further comprises imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

Generally, at least a portion of the oxidation reaction effluent is subjected to purification to remove at least part of the imide catalyst and the unreacted cyclohexylbenzene before passage to the cleavage step. Typically, all or a fraction of the oxidation reaction effluent initially undergoes treatment to reduce the level of the cyclic imide in the effluent to, for example, less than 100 ppmw, such as less than 20 ppmw. This is conveniently effected by contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. Another possible separation involves passage of all or a fraction of the oxidation effluent over a bed of solid sorbent. Suitable solid sorbents include alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes. An example of separation of cyclic imide by basic material treatment is disclosed in International Patent Publication No. WO 2009/025939.

After treatment to remove the cyclic imide catalyst, the oxidation effluent is maintained under conditions such that crystals of cyclohexylbenzene hydroperoxide form and separate from the treated reaction product. This is conveniently achieved by cooling the treated reaction product to a temperature between about 2° C. and about 10° C. and allowing the crystals to form, which normally takes from about 2 hours to about 170 hours. When crystallization is complete the cyclohexylbenzene hydroperoxide crystals can be recovered from the oxidation effluent and supplied to the cleavage step. The crystallization step can be performed one time or can be repeated several times to improve the yield of the cyclohexylbenzene hydroperoxide. The recovered cyclohexylbenzene hydroperoxide crystals typically have a purity of >85%, preferably >90%.

Hydroperoxide Cleavage

Another reactive step in the conversion of the cyclohexylbenzene into phenol and cyclohexanone involves the acid-catalyzed cleavage of the cyclohexylbenzene hydroperoxide recovered from the oxidation reaction effluent.

In one embodiment, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brøonsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon total weight of the cleavage reaction mixture.

In various embodiments, the cleavage catalyst may be zeolite beta, zeolite Y, ZSM-5 zeolite, ZSM-12 zeolite, and/or mordenite.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone.

Although the mechanism is not fully understood, it is believed that the polar solvent reduces the free radical inducted conversion of the cyclohexylbenzene hydroperoxide to undesired products such as hexanophenone and phenylcyclohexanol.

Suitable cleavage conditions include a temperature of at least 20° C. and no greater than 200° C., or at least 40° C. and no greater than 120° C., and a pressure of at least 1 psig and no greater than 370 psig (at least 7 kPa and no greater than 2,550 kPa, gauge), or at least 14.5 psig and no greater than 145 psig (at least 100 kPa and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product may contain unreacted acid catalyst and hence at least a portion of the cleavage reaction product may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay, such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate, and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites, and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

Uses of Cyclohexanone and Phenol

The cyclohexanone produced through the processes disclosed herein may be used, for example, as an industrial solvent, as an activator in oxidation reactions, and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the accompanying drawing.

Example 1

Figure 1A:
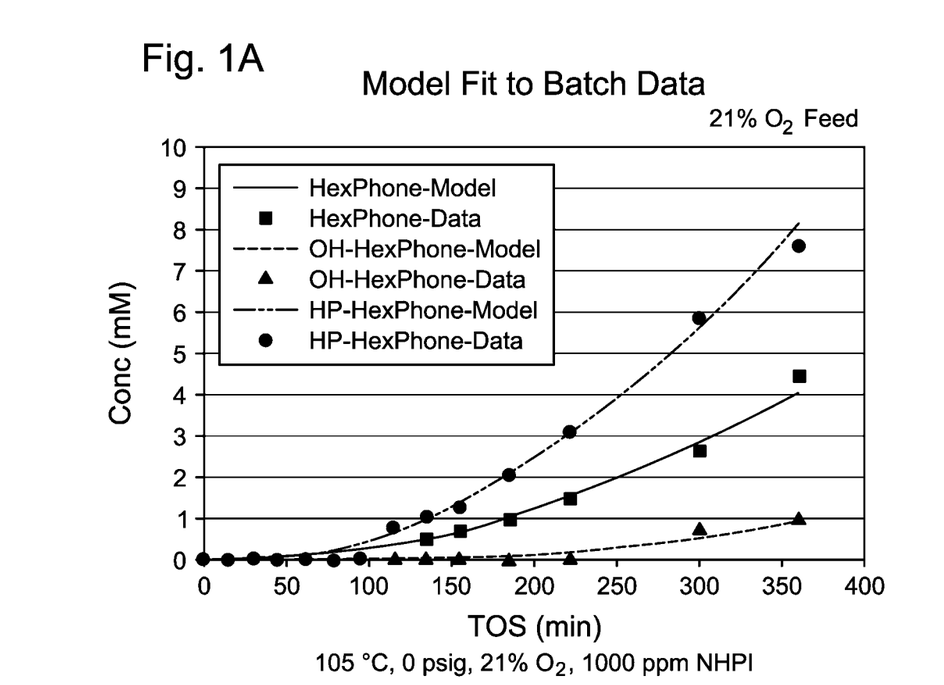
FIG. 1A is a graph illustrating the concentrations of 6-hydroperoxyhexaphenone, 6-hydroxyhexaphenone and 1-phenyl-1-hexaphenone over time in a cyclohexylbenzene oxidation reaction using an air feed containing 21 wt % of oxygen.

An oxidation reaction of cyclohexylbenzene and oxygen was conducted at a temperature of 105° C. and a pressure of 0 psi, gauge (0 kPa, gauge) using 1000 ppm of N-hydroxyphthalimide as the oxidation catalyst. The oxygen source was air containing 21 wt % oxygen, the wt % based upon the weight of the air. The concentrations (millimolar) of 6-hydroperoxyhexaphenone (HP-HexPhone), 6-hydroxyhexaphenone (OH-HexPhone), and 1-phenyl-1-hexaphenone (HexPhone) were tracked over time, and compared to the concentrations of these byproducts predicted by the kinetic model:

$$\beta' = k\left(\frac{[O_2]^2}{[\text{Cyclohexylbenzene}]}\right)$$

wherein $[O_2]$ is the molar concentration (mol/L) of the dissolved oxygen in the effluent, [cyclohexylbenzene] is the molar concentration (mol/L) of the cyclohexylbenzene in the effluent, and k is determined by the following equation:

$$k = e^{\wedge\left[\frac{15100}{T+273.15} - 30.055\right]}.$$

The results are shown in FIG. 1A.

Example 2

Example 1 was repeated using air containing 15 wt % oxygen, the wt % based upon the weight of the air. The results are shown in FIG. 1B.

Figure 1B:
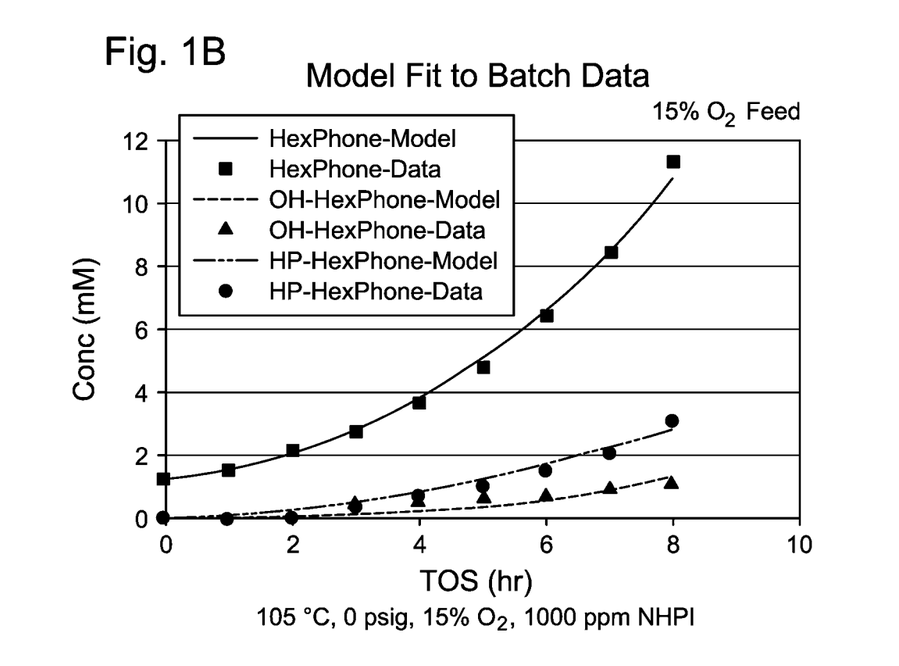
FIG. 1B is a graph illustrating the concentrations of 6-hydroperoxyhexaphenone, 6-hydroxyhexaphenone, and 1-phenyl-1-hexaphenone over time in a cyclohexylbenzene oxidation reaction using air containing 15 wt % of oxygen.
Figure 2:
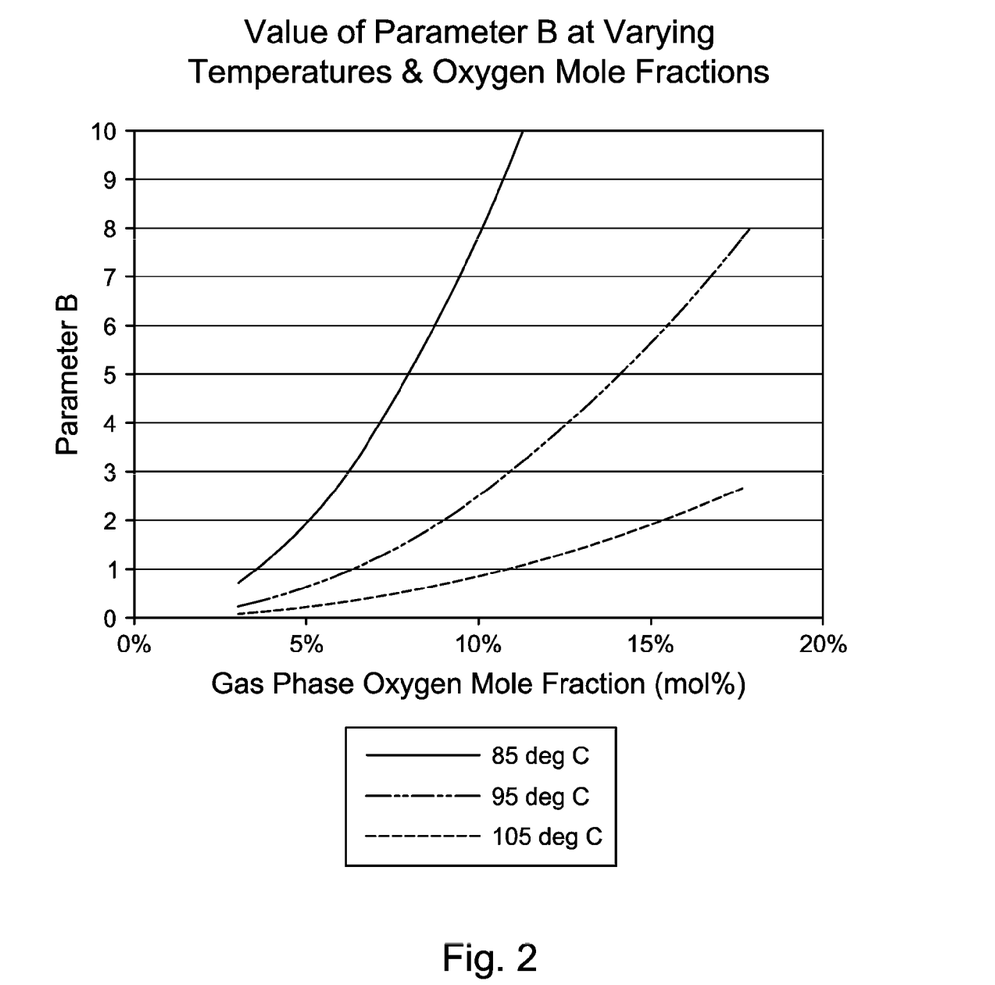
FIG. 2 is a graph illustrating the dependence of the ratio β on temperature.

FIGS. 1A and 1B show that the kinetic model accurately reflect the experimental values of the β-scission byproducts in the experimental data and its shifts with the amount of oxygen supplied to the reaction. FIGS. 1A and 1B show that the system forms more 6-hydroperoxyhexaphenone and 6-hydroxyhexaphenone with a 21 wt % oxygen feed and shifts to form more 1-phenyl-1-hexaphenone with a 15 wt % oxygen feed.

Example 3

An oxidation reaction of cyclohexylbenzene and oxygen was conducted at a variable temperature and a pressure of 0 kPa, gauge using 1000 ppm of N-hydroxyphthalimide as the oxidation catalyst. The oxygen source was air containing 21 wt % oxygen, the wt % based upon the weight of the air. As shown in FIG. 3, the value of β was determined at different temperatures to show the dependence of variable k on temperature.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. An oxidation process comprising:
   a) contacting a composition comprising cyclohexylbenzene and oxygen in at least one oxidation zone under oxidation conditions sufficient to produce an effluent comprising (i) cyclohexylbenzene hydroperoxide; (ii) a first byproduct that is indicative of a high dissolved oxygen content in the composition; and (iii) a second byproduct that is indicative of a low dissolved oxygen content in the composition;
   b) determining a ratio β according to the following formula:

$$\beta = \frac{A}{B}$$

wherein A is the amount of the first byproduct in the effluent, and B is the amount of the second byproduct in the effluent; and
   c) implementing an effect selected from (i) maintaining the ratio β above a threshold value; and (ii) adjusting the ratio β above a threshold value.

2. The process of claim 1, wherein the ratio β is correlated to the amount of oxygen dissolved in the composition.

3. The process of claim 1, wherein the amount of the first byproduct in the effluent is expressed as the concentration of the first byproduct in the effluent, and the amount of the second byproduct in the effluent is expressed as the concentration of the second byproduct in the effluent.

4. The process of claim 1, wherein the effect is adjusting the ratio β above a threshold value.

5. The process of claim 4, wherein the ratio β is adjusted by performing one or more of:
   A) increasing the amount of oxygen supplied to the contacting step (a);
   B) decreasing the temperature in the oxidation zone;
   C) increasing agitation in the oxidation zone; and
   D) increasing operating pressure of the oxidation zone to increase oxygen partial pressure in the gas phase.

6. The process of claim 1, further comprising repeating steps b) and c).

7. The process of claim 1, wherein at least one of the first byproduct and the second byproduct is formed from the decomposition of cyclohexylbenzene hydroperoxide.

8. The process claim 1, wherein at least a portion of the cyclohexylbenzene hydroperoxide decomposes into an alkoxy radical having the structure:

and at least one of the first byproduct and the second byproduct are formed from the alkoxy radical.

9. The process of claim 1, wherein the first byproduct contains more oxygen atoms than the alkoxy radical and the second byproduct contains the same or less number of oxygen atoms than the alkoxy radical.

10. The process of claim 1, wherein the first byproduct is selected from 6-hydroperoxyhexaphenone and 6-hydroxyhexaphenone.

11. The process of claim 1, wherein the second byproduct is selected from 1-phenyl-1-hexaphenone, 1-phenyl-1-hexenone, benzoic acid, and pentanal.

12. The process of claim 1, wherein the contacting step (a) produces at least some 6-hydroperoxyhexaphenone, 6-hydroxyhexaphenone, and 1-phenyl-1-hexaphenone in the effluent and β is equal to β', wherein β' is determined according to the following formula:

$$\beta' = \frac{[6\text{-hydroperoxyhexaphenone}] + [6\text{-hydroxyhexaphenone}]}{[1\text{-phenyl}-1\text{-hexaphenone}]},$$

where [6-hydroperoxyhexaphenone], [6-hydroxyhexaphenone], and [1-phenyl-1-hexaphenone] are the amounts of 6-hydroperoxyhexaphenone, 6-hydroxyhexaphenone, and 1-phenyl-1-hexaphenone respectively in the effluent.

13. The process of claim 1, wherein the threshold value is 0.1.

14. The process of claim 1, wherein the threshold value is 0.5.

15. The process of claim 11, wherein the concentration of dissolved oxygen in the composition [$O_2$] is determined from the following rate equation:

$$\beta' = k\left(\frac{[O_2]^2}{[\text{Cyclohexylbenzene}]}\right)$$

wherein [cyclohexylbenzene] is the molar concentration (mol/L) of the cyclohexylbenzene in the effluent, and k is determined by the following equation:

$$k = e^{\wedge\left[\frac{15100}{T+273.15} - 30.055\right]}$$

wherein T is the temperature of the contacting step (a) in degrees Celsius.

16. The process of claim 1, wherein the contacting (a) is conducted in the presence of an oxidation catalyst comprising a cyclic imide of the general formula (I):

(I)

wherein X represents an oxygen atom, a hydroxyl group, or an acyloxy group, and each of $R^7$, $R^8$, $R^9$, and $R^{10}$ is independently selected from H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I, and $NO_2$.

17. The process of claim 16, wherein the oxidation catalyst is N-hydroxyphthalimide.

18. The process of claim 1, wherein the ratio β is measured at more than one location in the effluent.

19. The process of claim 1, wherein the ratio β is determined on a continuous or semi-continuous basis.

20. The process of claim 1, wherein the oxidation conditions comprise a temperature of between about 70° C. and about 150° C. and a pressure of between about 0 kPa and about 500 kPa.

21. The process of claim 1, further comprising cleaving at least a portion of the cyclohexylbenzene hydroperoxide to produce phenol and cyclohexanone.

22. An oxidation process comprising:
   a) contacting cyclohexylbenzene with an oxygen-containing compound in at least one oxidation zone under oxidation conditions sufficient to form an effluent comprising at least some cyclohexylbenzene hydroperoxide, 6-hydroperoxyhexaphenone, 6-hydroxyhexaphenone, and 1-phenyl-1-hexaphenone;
   b) measuring the amounts of the 6-hydroperoxyhexaphenone, 6-hydroxyhexaphenone and 1-phenyl-1-hexaphenone in the effluent;
   c) determining a ratio β according to the following formula:

$$\beta = \frac{[6\text{-hydroperoxyhexaphenone}] + [6\text{-hydroxyhexaphenone}]}{[1\text{-phenyl}-1\text{-hexaphenone}]};$$

where [6-hydroperoxyhexaphenone], [6-hydroxyhexaphenone] and [1-phenyl-1-hexaphenone] are amounts of the respective components in the effluent; and
   d) adjusting the ratio β to above a threshold value.

23. The process of claim 22, wherein the threshold value is 0.1.

24. A process for producing phenol and cyclohexanone, the process comprising:
   (a) contacting benzene with hydrogen in the presence of a hydroalkylation catalyst under conditions effective to produce cyclohexylbenzene;
   (b) contacting at least a portion of the cyclohexylbenzene with oxygen in the presence of a cyclic imide catalyst under conditions effective to form an effluent comprising at least some cyclohexylbenzene hydroperoxide, 6-hydroperoxyhexaphenone, 6-hydroxyhexaphenone and 1-phenyl-1-hexaphenone, wherein at least a portion of the contacting step (a) is conducted at a ratio β of greater than 0.1, wherein β is determined according to the following formula:

$$\beta = \frac{[6\text{-hydroperoxyhexaphenone}] + [6\text{-hydroxyhexaphenone}]}{[1\text{-phenyl}-1\text{-hexaphenone}]},$$

wherein [6-hydroperoxyhexaphenone], [6-hydroxyhexaphenone], and [1-phenyl-1-hexaphenone] are molar concentrations of 6-hydroperoxyhexaphenone, 6-hydroxyhexaphenone, and 1-phenyl-1-hexaphenone respectively in the effluent; and
   (c) cleaving at least a portion of the cyclohexylbenzene hydroperoxide produced in (b) to produce phenol and cyclohexanone.

25. The process of claim 24, wherein the contacting (b) is conducted in a plurality of reaction zones connected in series and the ratio β is determined in at least two of the plurality of reaction zones.

\* \* \* \* \*